United States Patent [19]
Cosmescu

[11] Patent Number: 5,199,944
[45] Date of Patent: * Apr. 6, 1993

[54] AUTOMATIC SMOKE EVACUATOR SYSTEM FOR A SURGICAL LASER APPARATUS AND METHOD THEREFOR

[76] Inventor: Ioan Cosmescu, 14449 N. 22nd St., Phoenix, Ariz. 85022

[*] Notice: The portion of the term of this patent subsequent to Apr. 28, 2009 has been disclaimed.

[21] Appl. No.: 764,842

[22] Filed: Sep. 24, 1991

Related U.S. Application Data

[63] Continuation-in-part of Ser. No. 527,589, May 23, 1990, Pat. No. 5,108,389.

[51] Int. Cl.$^5$ .................................................. A61B 17/36
[52] U.S. Cl. ........................................ 604/26; 604/23; 606/10; 128/747
[58] Field of Search ...................... 604/23–28, 604/30, 35, 21; 606/10; 128/747

[56] References Cited

U.S. PATENT DOCUMENTS

| | | | |
|---|---|---|---|
| 4,207,887 | 6/1980 | Hiltbrandt et al. | 604/26 |
| 4,648,386 | 3/1987 | Morritt et al. | 604/25 |
| 4,715,372 | 12/1987 | Philippbar et al. | 606/10 |
| 4,735,603 | 4/1988 | Goodson et al. | 604/35 |
| 4,735,606 | 4/1988 | Davison | 604/28 |
| 4,850,352 | 7/1989 | Johnson | 604/35 |
| 4,966,578 | 10/1990 | Baier et al. | 604/26 |
| 4,971,034 | 11/1990 | Doi et al. | 606/10 |
| 5,013,294 | 5/1991 | Bair | 604/26 |
| 5,108,389 | 4/1992 | Cosmescu | 606/10 |

Primary Examiner—Ralph Lewis
Attorney, Agent, or Firm—Harry M. Weiss

[57] ABSTRACT

A smoke evacuator system for use during laser surgery is disclosed. In the case of a laser laparoscope, the laparoscope is provided with a conduit and fitting to provide $CO_2$ gas through the laparoscope for distension purposes. The laser laparoscope is coupled to a special trocar that has exhaust holes near the tip (inside the body cavity) that are connected via conduit to an external fitting (outside the body cavity) to allow a vacuum source to draw smoke and $CO_2$ gas out of the body cavity. The smoke evacuator system can use either a built-in vacuum pump or an external vacuum source such as that typically provided in an operating room. Electronics are provided which detect the activation of the cutting laser beam of the laser laparoscope, and activate the smoke evacuator system accordingly. In this manner the smoke evacuator system is turned on automatically each time the surgeon activates the cutting laser beam of the laser laparoscope. This smoke evacuation system has the advantages of not requiring an addition incision and not requiring additional personnel to operate the system.

47 Claims, 2 Drawing Sheets

AUTOMATIC SMOKE EVACUATOR SYSTEM FOR A SURGICAL LASER APPARATUS AND METHOD THEREFOR

RELATED APPLICATION

This patent application is a continuation-in-part of my earlier patent application entitled "AUTOMATIC SMOKE EVACUATOR ACTIVATOR SYSTEM FOR A SURGICAL LASER APPARATUS AND METHOD THEREFOR", Ser. No. 07/527,589, filed May 23, 1990, now U.S. Pat. No. 5,108,389 and is incorporated herein by reference thereto.

FIELD OF THE INVENTION

This invention generally relates to smoke evacuator systems and methods therefor, and more specifically relates to an automatic smoke evacuator system for a surgical laser apparatus and method therefor which is automatically activated when the laser cutting beam of a surgical laser apparatus is turned on, which does not require additional incisions in the patient, and which can be used without additional personnel or procedures for the removal of smoke during laser surgery.

DESCRIPTION OF THE PRIOR ART

U.S. Pat. No. 4,735,603 discloses a laser smoke evacuation system and method. This system provides a $CO_2$ insufflator attached to a laser laparoscope to maintain the appropriate distention of the body cavity of the patient during surgery, and a separate vacuum source for removing the smoke from the body cavity. This system requires at least one additional incision in the patient for the vacuum source. The vacuum source removes $CO_2$ from the body that is contaminated with smoke, water vapor, and debris. This contaminated $CO_2$ is filtered and recycled to the $CO_2$ insufflator, which pumps the recycled $CO_2$ once again into the body cavity of the patient.

The vacuum source is a separate instrument and requires an additional incision in the patient so the vacuum source can be placed in the body cavity in proximity to the surgical procedure being performed. This incision causes additional pain to the patient. An additional medical person is needed to appropriately place the vacuum source and assure its proper location throughout the surgical procedure, adding significant expense to the laser surgical procedure. This type of smoke evacuator system is generally turned on manually and operated continuously during a laser surgical procedure. This continuous operation of the smoke evacuator system during surgery produces a constant noise and uses electrical power. In addition the continuous air pressure on the filter element of the smoke evacuator system usually saturates or overloads the system's filter element and thereby allows the toxic fumes which are supposed to be evacuated from the surgical area to escape uncontrolled into the medical operating room rather than being vented outside, which is supposed to be the function of the smoke evacuator system.

Therefore, there existed a need to provide an automatic smoke evacuator system which can be used in conjunction with a laser surgical tool, requiring no additional incision in the patient, and which is activated automatically when the cutting laser beam is activated.

SUMMARY OF THE INVENTION

It is an object of this invention to provide an automatic smoke evacuator system and method to remove smoke from the body cavity during a laser surgical procedure.

It is another object of this invention to provide an automatic smoke evacuator system and method for use during laser laparoscopy or electro surgical laparoscopy.

It is a further object of this invention to provide an automatic smoke evacuator system and method that is activated automatically when the laser cutting beam of the laser surgical tool is activated.

It is still another object of this invention to provide an automatic smoke evacuator system and method which requires no additional incision, no additional medical personnel for its operation, and no additional steps in the surgical process to effectively eliminate smoke during a laser surgical procedure.

It is yet further object of this invention to provide an automatic smoke evacuator system and method which can use either an external vacuum source, or an internal vacuum source provided with the smoke evacuator system.

According to the present invention, a laser surgical tool is provided. For illustrative purposes, this laser surgical tool is a laser laparoscope for the disclosure herein. This laparoscope is equipped with an external fitting which is normally connected to a $CO_2$ insufflator. The $CO_2$ is pumped through the fitting to the end of the surgical tool inside the body cavity, which distends the body cavity of the patient. The laparoscope is placed through a special trocar which has a hollow conduit that runs from the tip of the trocar to a fitting located on the portion of the trocar that is external to the body cavity. This fitting is connected to a vacuum source. The smoke evacuator system has various external elements which are used to monitor pressure in the body cavity, control the flow of the $CO_2$ to the laser surgical tool, control the flow to the vacuum source from the laser surgical tool, and activate the smoke evacuator system when the cutting laser beam is activated. The optical sensors are installed on the foot switch the surgeon normally uses to activate the cutting laser beam which causes the foot switch to also control the activation of the smoke evacuator system.

By using the smoke evacuator system of the present invention, a flow of $CO_2$ gas in the direction of the laser beam is created automatically every time the foot switch is activated which controls the laser cutting beam. At the same time the vacuum source removes the smoke and water vapor from the body cavity through the special trocar thereby improving the quality of the laser beam, since smoke and water vapor can absorb and diverge the laser beam. In this manner the removal of smoke is completely automatic, requiring no additional incision and no additional personnel to operate the smoke evacuator system.

The foregoing and other objects, features and advantages will be apparent from the following description of the preferred embodiment of the invention as illustrated in the accompanying drawings.

DESCRIPTION OF THE PREFERRED EMBODIMENT

Figure 1:
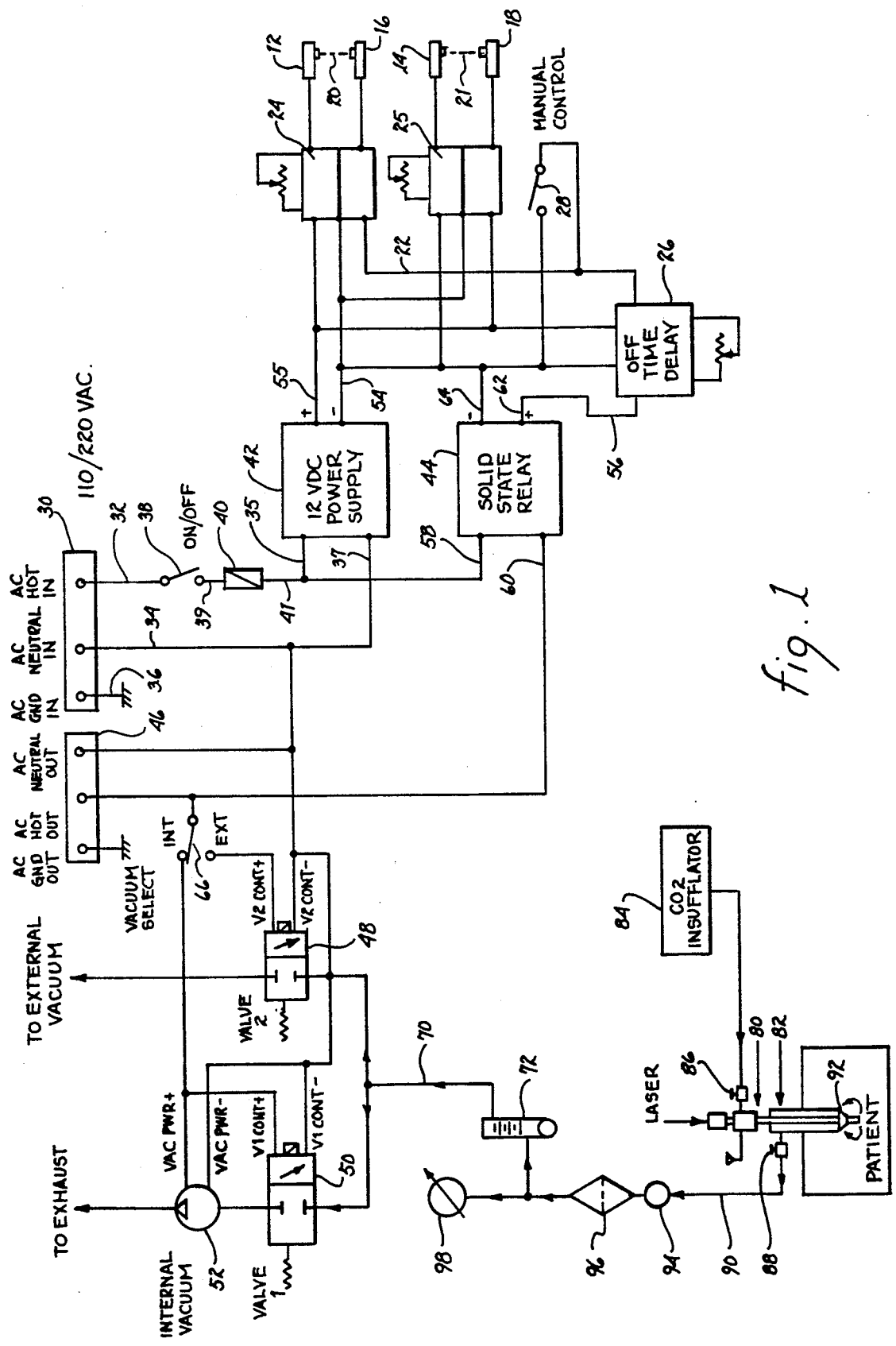
FIG. 1 is a schematic block diagram of the automatic smoke evacuator system of the present invention.

Referring to FIG. 1, the schematic block diagram for the automatic smoke evacuator system of the present invention is shown. A conventional Alternating Current (AC) power source is coupled to input connector 30 to provide source power for the smoke evacuator system. This AC source provides AC HOT IN (32), AC NEUTRAL IN (34), and AC GROUND IN (36) as shown.

AC HOT IN (32) is connected to an ON/OFF switch 38. The other side of ON/OFF switch 38 is switched power 39, which is connected to a fuse 40. The other side of fuse 40 is fused power 41, which is connected to the positive input 35 of the 12 VDC Power Supply 42 as shown, and to the input 58 of Solid State Relay 44.

AC NEUTRAL IN (34) is connected to the negative input 37 of the 12 VDC Power Supply 42, to the output connector 46, to the negative control inputs on solenoid valves 48 and 50, and to vacuum pump 52 as shown.

AC GROUND IN (36) is connected to the chassis of the Smoke Evacuator System and to output connector 46 as shown.

Solid State Relay 44 serves to switch the fused power 41 from its input terminal 58 to its output terminal 60 when a logical high is present between control terminals 62 and 64. This switched power 60 is what powers the vacuum pump 52 and solenoid valves 48 and 50 that control the flow of smoke and $CO_2$ gas out of the body cavity. Vacuum Select switch 66 is used to select either an external vacuum source or the Internal Vacuum 52 within the smoke evacuator system. As shown in the schematic, when Vacuum Select switch 66 is in the INTERNAL position, the output 60 of Solid State Relay 44 is connected to the Internal Vacuum 52 and to the positive control terminal of Valve 1 (50). When Vacuum Select switch 66 is in the EXTERNAL position, the output 60 of Solid State Relay 44 is connected to the positive control terminal of Valve 2 (48).

The negative output 54 of the 12 VDC Power Supply 42 is connected to the negative power inputs of optical sensor 24, optical sensor 25, Solid State Relay 44, Off Time Delay timer 26, and to Manual Control switch 28 as shown. The positive output 55 of the 12 VDC Power Supply 42 is connected to the positive power inputs of optical sensor 24, optical sensor 25, and Off Time Delay timer 26, as shown.

This system includes optical transmitters 12 and 14, with associated optical receivers 16 and 18. Optical transmitter 12 sends an optical beam 20 to optical receiver 16. In like manner optical transmitter 14 sends an optical beam 21 to optical receiver 18. Optical transmitters 12 and 14 and optical receivers 16 and 18 are all mounted to the foot switch of the laser cutting beam in such a way as to interrupt the beams 20 and 21 when the foot switch is in certain positions. The presence or absence of the optical beam 20 on optical receiver 16 generates a control signal output 22 on optical sensor 24. This control signal output 22 is used to control the Off Time Delay timer 26. Optical sensor 25 operates in relation to optical transmitter 16 and optical receiver 18 in like fashion.

The control signal output 22 of optical sensors 24 and 25 is used to trigger the Off Time Delay timer 26. When the foot switch of the laser cutting beam is depressed by the surgeon, the control signal output 22 causes the timer output 56 to go to a logical high. This high signal on the positive control input 62 of Solid State Relay 44 causes the Solid State Relay 44 to switch the fused AC HOT signal on its input 58 to its output 60. This causes the valve selected by Vacuum Select switch 66 to open. (Both Valve 1 (50) and Valve 2 (48) are normally closed.) If Vacuum Select switch 66 is in the INTERNAL position, the opening of Valve 1 (50) is accompanied by the activation of Internal Vacuum 52. If Vacuum Select switch 66 is in the EXTERNAL position, Valve 2 (48) is opened. In either case power is switched to the output connector 46 to power an external vacuum source, if needed. Whether the vacuum source is internal or external to the smoke evacuator system, a vacuum is created in Vacuum Line 70.

Note that the Manual Control switch 28 can be used to bypass the optical sensors 24 and 25 and generate the control signal output 22 directly. This allows the smoke evacuator system to start another smoke exhaust cycle for applications that may require this feature.

The Off Delay Timer 26 provides a time delay so the vacuum in line 70 is maintained for a period of time after the foot switch for the cutting laser beam has been released. This delay provides exhaust after the cutting has stopped to assure all the smoke has been evacuated.

A laparoscope 80 is shown with associated trocar 82. The laser for the laser laparoscope 80 is not shown. The laparoscope 80 has a stopcock 86 for connecting to the $CO_2$ insufflator 84. The trocar 82 has a stopcock 88 for connection to a vacuum line 90. This stopcock 88 is connected to several holes 92 at the bottom of trocar 82 which provide the exhaust path for the smoke evacuator system.

Vacuum line 90 is connected to a water trap 94 and a filter 96, which remove most of the contaminants from the exhaust stream. Pressure gauge 98 is used to monitor the pressure in the body cavity, and adjustable flow meter 72 is used to regulate the exhaust flow to an appropriate level.

Figure 2:
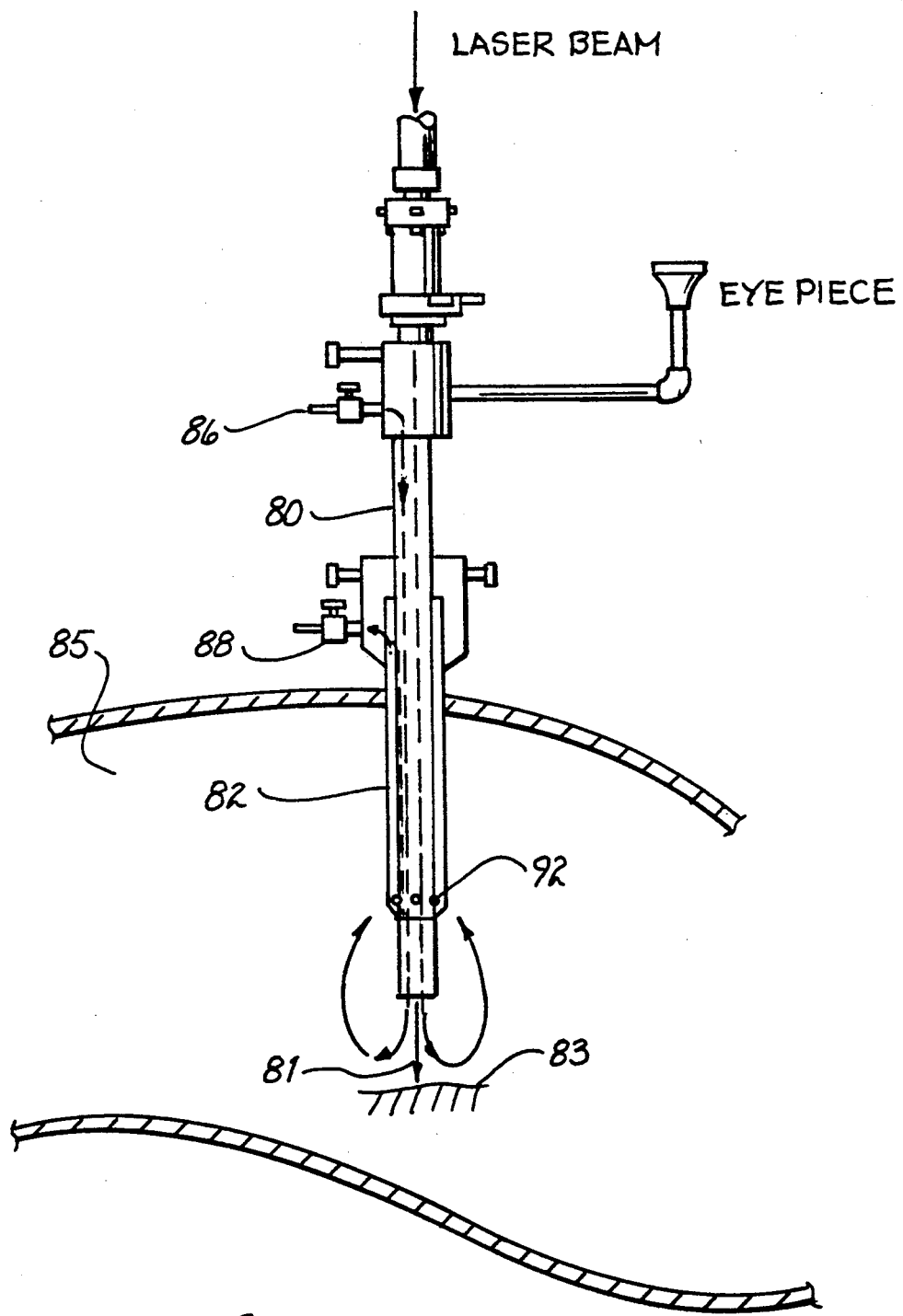
FIG. 2 is a side view of the laser laparoscope and special trocar used as part of the automatic smoke evacuator system shown in FIG. 1, shown in use in a body cavity during a laser surgical procedure.

FIG. 2 shows the laser laparoscope 80 equipped with the trocar 82. As shown in FIG. 1, stopcock 86 is connected to the $CO_2$ insufflator 84, and stopcock 88 is connected to vacuum line 90. As shown in FIG. 2, when the laser cutting beam 81 is activated, the cutting of the tissue 83 with the laser beam can produce smoke and water vapor. The activation of the cutting laser beam causes the smoke evacuator system to be activated automatically. When the smoke evacuator system is activated, vacuum line 90 presents a vacuum to stopcock 88, which draws smoke and $CO_2$ gas through exhaust holes 92 from the body cavity 85 of the patient. This drop in pressure allows $CO_2$ to flow from the insufflator through stopcock 86 and to the end of the laparoscope 80 as shown. At the same time smoke and water vapor are going out the exhaust holes 92 due to the vacuum in line 90. This flow of fresh $CO_2$ to the tissue 83 and up to exhaust holes 92 helps keep the lens in laser laparoscope 80 from being contaminated by smoke, water vapor, and debris, improving the performance of the laser laparoscope 80.

OPERATION

Using the smoke evacuator system is transparent to the surgeon's normal activities once the system is connected and ready for use. The surgeon uses the trocar which is provided with exhaust holes 92 connected to stopcock 88. This stopcock 88 is connected to vacuum line 90 as shown. The surgeon then places the laser laparoscope in the trocar, and the smoke evacuation occurs during surgery automatically every time the cutting laser beam is activated.

If the operating room has a vacuum source available, this vacuum source is coupled to the output of Valve 2 (48). Vacuum Select switch 66 on the smoke evacuator system is then placed in the EXTERNAL position, since a vacuum source external to the system is being used. This makes the Solid State Relay 44 activate Valve 2 (48) when smoke evacuation is needed. At the same time AC power is switched to output connector 46 which can be connected to the power cord of the external vacuum source.

If the operating room does not have a convenient vacuum source available, or if the surgeon desires to use the vacuum source internal to the system, the Vacuum Select switch 66 is placed in the INTERNAL position. This makes the solid state relay activate the Internal Vacuum 52 and Valve 1 (50) simultaneously when smoke evacuation is needed.

When the surgeon presses the foot switch to activate the cutting laser beam, at least one of the optical sensors 24 and 25 sense the movement of the foot switch and generate the control signal 22. This control signal 22 triggers the Off Delay Timer 26, which drives the control input 62 of Solid State Relay 44 high. This causes Solid State Relay 44 to switch AC power to the valve selected by the Vacuum Select switch 66. This AC power on the input to the valve causes the valve to open. The opening of the appropriate valve causes the resultant vacuum to cause smoke and gas within the body cavity to flow to the holes in trocar 82, out stopcock 88, through vacuum line 90, through water trap 94 and filter 96, through adjustable flow meter 72, through vacuum line 70, and through the solenoid valve 48 or 50 selected by Vacuum Select switch 66, to an exhaust port. When the surgeon stops depressing the foot switch controlling the laser cutting beam, control signal 22 is negated, causing Off Delay Timer 26 to begin its timing sequence, maintaining the vacuum on line 70 for some time period after control signal 22 has been negated. In this manner all residual smoke is removed after cutting has stopped, assuring complete smoke evacuation with each activation of the laser cutting beam.

Since the smoke evacuation system of the present invention is activated only when the laser cutting beam is activated, the smoke evacuator system is only on for a small portion of the time the patient is in surgery. For this reason the $CO_2$ gas that is removed from the patient by the vacuum source does not need to be recycled. In the prior art smoke evacuator system, the system is operated continuously during surgery, making the recovery and recycling of the contaminated $CO_2$ desirable. However, with the smoke evacuator system of the present invention, such small quantities of $CO_2$ are used that the contaminated $CO_2$ can be filtered and disposed of out the exhaust port. This method assures the smoke eliminator system cannot transfer any contaminated matter to the patient undergoing the procedure, or to the next patient whose surgery requires the use of the smoke evacuator system.

While the invention has been described in its preferred embodiment, it is to be understood that the words which have been used are words of description rather than limitation, and that changes may be made within the purview of the appended claims without departing from the true scope and spirit of the invention in its broader aspects. For example, a different laser surgical tool, such as a laser dental surgical tool, could be used.

I claim:

1. An automatic smoke evacuator system and an external laser surgical apparatus comprising, in combination:
    a laser surgical apparatus with a conduit for carrying gas;
    flow means coupled to said laser surgical apparatus to provide a flow of gas through said conduit in said laser surgical apparatus;
    exhaust means for carrying gas coupled to said laser surgical apparatus to withdraw gas from the area of the laser surgical apparatus;
    vacuum means for providing a gas flow force for said exhaust means;
    gas carrying conduit assembly means for connecting said exhaust means to said vacuum means;
    electrically actuated valve means for controlling flow in said gas carrying conduit assembly means;
    control means for activating said valve means in response to the activation of said laser surgical apparatus.

2. The system of claim 1 wherein said laser surgical apparatus comprising a laser laparoscope.

3. The system of claim 1 wherein said flow means comprising a carbon dioxide ($CO_2$) insufflator.

4. The system of claim 1 wherein said exhaust means comprising a trocar having at least one exhaust hole on the end that is to be inserted into a body cavity, the trocar having a lumen connecting said at least one exhaust hole to a fitting on the end of said trocar that is to be external to the body cavity and connected to said gas carrying conduit assembly means.

5. The system of claim 1 wherein said vacuum means comprising a vacuum pump contained within said smoke evacuator system.

6. The system of claim 1 wherein said vacuum means comprising a vacuum source external to said smoke evacuator system.

7. The system of claim 1 wherein said valve means comprising at least one solenoid-actuated valve controlled by said control means.

8. The system of claim 7 wherein said solenoid-actuated valve is normally closed.

9. The system of claim 1 wherein said gas carrying conduit assembly means comprising a vacuum conduit having a water trap.

10. The system of claim 9 wherein said gas carrying conduit assembly means further comprising a filter element in said vacuum conduit.

11. The system of claim 10 wherein said gas carrying conduit assembly means further comprising an adjustable flow meter in said vacuum conduit.

12. The system of claim 11 wherein said gas carrying conduit assembly means further comprising a pressure gauge in said vacuum conduit.

13. The system of claim 1 wherein said control means comprises, in combination:
    power input means;
    at least one control switch means for detecting activation of said laser surgical apparatus, with an output having two electrical states;
    power switch means for switching power to said valve means and to said vacuum means in response to a control signal generated by said control switch means.

14. The system of claim 13 wherein said power input means comprising a three conductor power cord having a plug that couples said cord to a conventional power outlet for alternating current (AC).

15. The system of claim 13 further comprising direct current (DC) voltage regulation means.

16. The system of claim 13 wherein said control switch means comprises an optical sensor having an optical transmitter and optical receiver, said output being in one of said two electrical states when the optical beam between said transmitter and said receiver is uninterrupted, which output changes to the second of said two electrical states when said optical beam is interrupted.

17. The system of claim 16 wherein said control switch means is mechanically coupled to a switch that activates said laser surgical apparatus such that actuation of said switch causes said output of said control switch means to change state.

18. The system of claim 17 wherein said switch that activates said laser surgical apparatus being a foot switch.

19. The system of claim 16 wherein said output of said control switch means can be used to start a new smoke exhaust cycle.

20. The system of claim 13 further comprising timer means for delaying the deactivation of said power switch means.

21. The system of claim 13 wherein said power switch means comprising a solid state relay.

22. The system of claim 13 further comprising switched power output means for powering a vacuum source external to said smoke evacuator system, which switched power output means is provided by the output of said power switching means.

23. The system of claim 13 further comprising vacuum select switch means which electrically connects the electrical control input on one of said valve means to the output of said power switch means when said vacuum select switch means is in one state, and which connects the electrical control input on a second of said valve means to the output of said power switch means when said vacuum select switch is in a second state.

24. A method for evacuating smoke out of a body cavity during a laser surgical procedure using a smoke evacuator system comprising of the steps of:
providing a laser surgical apparatus with a conduit for carrying gas;
providing flow means coupled to said laser surgical apparatus to provide a flow of gas through said conduit in said laser surgical apparatus;
providing exhaust means for carrying gas coupled to said laser surgical apparatus to withdraw gas from the area of the laser surgical apparatus;
providing vacuum means for providing a gas flow force for said exhaust means;
providing gas carrying conduit assembly means for connecting said exhaust means to said vacuum means;
providing electrically actuated valve means for controlling flow in said gas carrying conduit assembly means;
providing control means for activating said valve means in response to the activation of said laser surgical apparatus.

25. The method of claim 24 wherein said laser surgical apparatus comprising a laser laparoscope.

26. The method of claim 24 wherein said flow means comprising a carbon dioxide ($CO_2$) insufflator.

27. The method of claim 24 wherein said exhaust means comprising a trocar having at least one exhaust hole on the end that is inserted into a body cavity, the trocar having a lumen connecting said at least one exhaust hole to a fitting on the end of said trocar that is external to the body cavity and connected to said gas carrying conduit assembly means.

28. The method of claim 24 wherein said vacuum means comprising a vacuum pump contained within said smoke evacuator system.

29. The method of claim 24 wherein said vacuum means comprising a vacuum source coupled to said smoke evacuator system.

30. The method of claim 24 wherein said valve means comprising at least one solenoid-actuated valve controlled by said control means.

31. The method of claim 30 wherein said solenoid-actuated valve is normally closed.

32. The method of claim 24 wherein said gas carrying conduit assembly means comprising a vacuum conduit having a water trap.

33. The method of claim 32 wherein said gas carrying conduit assembly means further comprising a filter element in said vacuum conduit.

34. The method of claim 33 wherein said gas carrying conduit assembly means further comprising an adjustable flow meter in said vacuum conduit.

35. The method of claim 34 wherein said gas carrying conduit assembly means further comprising a pressure gauge in said vacuum conduit.

36. The method of claim 24 wherein said control means comprises, in combination:
power input means;
at least one control switch means for detecting activation of said laser surgical apparatus, with an output having two electrical states;
power switch means for switching power to said valve means and to said vacuum means in response to a control signal generated by said control switch means.

37. The method of claim 36 wherein said power input means comprising a three conductor power cord having a plug that couples said cord to a conventional power outlet for alternating current (AC).

38. The method of claim 36 further comprising direct current (DC) voltage regulation means.

39. The method of claim 36 wherein said control switch means comprises an optical sensor having an optical transmitter and optical receiver, said output being in one of said two electrical states when the optical beam between said transmitter and said receiver is uninterrupted, which output changes to the second of said two electrical states when said optical beam is interrupted.

40. The method of claim 39 wherein said control switch means is mechanically coupled to a switch that activates said laser surgical apparatus such that actuation of said switch causes said output of said control switch means to change state.

41. The method of claim 40 wherein said switch that activates said laser surgical apparatus being a foot switch.

42. The method of claim 39 wherein said output of said control switch means can be used to start a new smoke exhaust cycle.

43. The method of claim 36 further comprising timer means for delaying the deactivation of said power switch means.

44. The method of claim 36 wherein said power switch means comprising a solid state relay.

45. The method of claim 36 further comprising switched power output means for powering a vacuum source external to said smoke evacuator system, which switched power output means is provided by the output of said power switching means.

46. The method of claim 36 further comprising vacuum select switch means which electrically connects the electrical control input on one of said valve means to the output of said power switch means when said vacuum select switch means is in one state, and which connects the electrical control input on a second of said valve means to the output of said power switch means when said vacuum select switch is in a second state.

47. The method of claim 24 further comprising the steps of:

inserting said laser surgical apparatus with attached exhaust means into the body cavity where the surgery is to occur;

activating said laser surgical apparatus, which activation causes said valve means and said vacuum means to be activated, creating a path for exhaust gasses through said exhaust means, through said gas carrying conduit means, through said valve means, and through said vacuum means.

* * * * *